Figure 1:
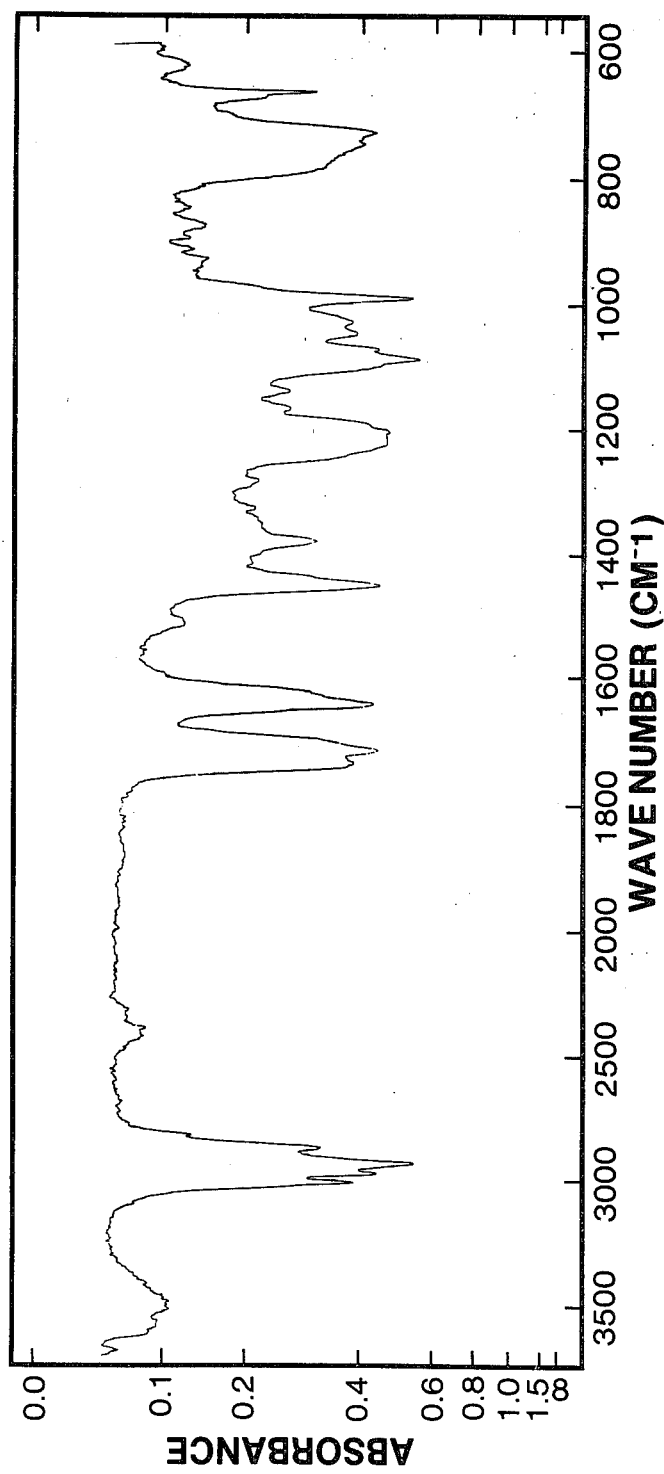

ately 25° and about 50° C. and then removing AY24,668 from the culture medium.

United States Patent [19]
Sehgal et al.

[11] 4,375,464
[45] Mar. 1, 1983

[54] ANTIBIOTIC AY24,668 AND PROCESS OF PREPARATION

[75] Inventors: Surendra N. Sehgal, Beaconsfield; Claude Vezina, Oka, both of Canada

[73] Assignee: Ayerst, McKenna & Harrison Inc., Montreal, Canada

[21] Appl. No.: 323,006

[22] Filed: Nov. 19, 1981

[51] Int. Cl.$^3$ .......................... A61K 35/00; C12P 1/06
[52] U.S. Cl. .................................... 424/122; 435/169
[58] Field of Search .......................... 424/122; 435/169

[56] References Cited

U.S. PATENT DOCUMENTS 3,929,992 12/1975 Sehgal et al. ........................ 424/122
3,993,749 11/1976 Sehgal et al. ........................ 424/122

OTHER PUBLICATIONS

A. Aszalos et al., J. Antibiotics, 21 611 (1968).
J. J. Armstrong et al., Nature, 206, 399 (1965).
C. Coronelli et al., J. Antibiotics, 20, 329 (1967).
S. Aizawa et al., J. Antibiotics, 24, 393 (1971).
G. Nesemann et al., Naturwissenschaften, 59, 81 (1972).
C. Vezina et al., J. Antibiotics, 28, 721 (1975).
S. N. Sehgal et al., J. Antibiotics, 28, 727 (1975).
H. Baker et al., J. Antibiotics, 32, 539 (1978).
R. R. Martel et al., Can. J. Physiol., 55, 48 (1977).

Primary Examiner—Jerome D. Goldberg
Attorney, Agent, or Firm—Arthur E. Wilfond

[57] ABSTRACT

Antibiotic AY24,668 is producible by culturing *Streptomyces hygroscopicus* NRRL 5491 in an aqueous nutrient medium. AY24,668 has antifungal properties. Methods for its preparation and use are disclosed.

3 Claims, 2 Drawing Figures

ANTIBIOTIC AY24,668 AND PROCESS OF PREPARATION

BACKGROUND OF THE INVENTION a. Field of the Invention

This invention relates to an antibiotic, a new composition of matter called AY24,668, and to a process for its preparation. AY24,668 is useful as an antifungal agent.

b. Description of the Prior Art

The antibiotic of this invention is readily distinguished from prior art compounds of its class by its profound antifungal activity and its relatively low order to toxicity.

More explicitly, the ultra violet spectrum of AY24,668, noted herein, indicates that this compound belongs to the class of antibiotics known as triene antibiotics. In this particular class there are only six compounds reported previously. Trienine, A. Aszalos et al., J. Antibiotics, 21,611 (1968) is a triene antibiotic with antitumor activity which also shows marked activity against gram positive organisms and only marginal activity against Candida strains. The antifungal triene reported by J. J. Armstrong, et al., Nature, 206, 399 (1965) and Mycotrienin reported by C. Coronelli et al., J. Antibiotics, 20, 329 (1967), representing the second and third antibiotic, are probably identical. Both have low antifungal activity (MIC against *Candida Albicans:* 5 $\mu$g/ml) and high toxicity (LD$_{50}$ in mice: 15 mg/kg). The fourth and fifth antibiotics-Resistaphylin, S. Aezaiva et al., J. Antibiotics, 24, 393 (1971) and Proticin, G. Nesemann et al., Naturwissenschaften, 59, 81 (1972) are readily distinguished from the compound of the present invention in that they exhibit antibacterial without any antifungal activity.

The sixth triene is antifungal rapamycin which is distinctly different from AY24,668 as indicated by comparison of their NMR spectra. Both may be structuraly related. Rapamycin is an antifungal antibiotic described by C. Vezina et al., J. Antibiot., 28, 721 (1975), S. N. Sehgal et al., J. Antibiot., 28, 727 (1975), S. N. Sehgal et al., U.S. Pat. No. 3,929,992, issued Dec. 30, 1975 and S. N. Sehgal et al., U.S. Pat. No. 3,993,749, issued Nov. 23, 1976. The latter two patents are herein incorporated by reference. Rapamycin is extracted from a streptomycete (*Streptomyces hygroscopicus*) isolated from an Easter Island soil sample and is particularly effective against *Candida albicans* both in vitro and in vivo, H. A. Baker et al., J. Antibiot., 31, 539 (1978).

Although AY24,668 is produced by the same microorganism as rapamycin, AY24,668 lacks the immunosuppressant activity of rapamycin [R. R. Martel et al., Can. J. Physiol., 55, 48 (1977)], and, therefore, is better suited for use as an antifungal agent.

SUMMARY OF THE INVENTION

AY24,668 is a chemical compound producible by culturing an AY24,668 producing organism in an aqueous nutrient medium. The compound has the property of adversely affecting the growth of fungi, for example, *Candida albicans.* Accordingly, AY24,668 may be used to prevent the growth of or reduce the number of fungi in various environments.

A convenient form for administering AY24,668 involves a pharmaceutical composition of AY24,668 and a pharmaceutically acceptable carrier.

DETAILS OF THE INVENTION

The AY24,668-producing organism used for this invention, *Streptomyces hydroscopicus* NRRL 5491, was obtained from Easter Island soils and samples thereof have been deposited without restrictions with the Northern Utilization and Research Division, Agricultural Research Service, U.S. Department of Agriculture, Peoria, Ill., U.S.A.

It is to be understood that the invention is not limited to the use of the particular organism herein described, but includes variations and mutants obtained by natural selection or by treatment of the microorganism with, for instance, ultraviolet rays, X-rays, N-methyl-N'-nitro-N-nitrosoguanidine, manganese chloride, camphor, nitrogen mustards, and the like, as well as polyploids of the various mutants.

*Streptomyces hygroscopicus* NRRL 5491 develops abundantly in culture media usually employed for cultivation of other organisms of the same genus. It is capable of growing at temperatures ranging from 20° to 35° C., preferably at about 28° C., on Czapek's agar, glucose asparagine agar, glycerol asparagine agar, starch agar and peptone beef agar. Also, the organism grows very well on yeast extract agar, malt extract agar, starch-inorganic salts agar, oatmeal agar, oatmeal-tomato agar and Bennet's agar. On potato slices there is no aerial mycelium, but substrate growth is well developed and buff in color. On all media, the aerial growth is at first white then grayish with black spots. Sporophores are often compact, forming a spiral of more than ten spores. Substrate growth is light yellow to almost colorless and in some media pale brown. Occasionally a yellowish pigment is produced. The organism is H$_2$S- and melanine-negative.

Carbohydrate utilization by *Streptomyces hygroscopicus* NRRL 5491 was studied in carbon utilization agar (ISP Medium 9) according to the procedure standardized by the International Streptomyces Project (SIP).

The best utilized carbohydrates were D-glucose, inositol, D-fructose and D-mannitol; less well utilized carbohydrates were rhamnose, raffinose, xylose, starch and arabinose. Carbohydrates not utilized were sucrose and cellulose.

The environment and nutritional requirements for the fermentation of *Streptomyces hydroscopicus* NRRL 5491 are similar to those necessary for the production of antibiotics by other aerobic microorganisms. Thus, aerobiosis can be sustained in a liquid nutrient medium inoculated with a sterile culture incubated in flasks placed on shaking machines. For industrial production, metal tanks with internal aeration and agitation by means of paddles can be substituted. AY24,668 is also produced by surface cultivation. The microorganism requires as nutrient elements assimilable carbon and organic nitrogenous substances. The presence of mineral salts is desirable. Cultivation is best effected when the initial pH of the culture medium is between 5.8 and 7.5, the optimum pH being around 6.0 to 7.3.

The utilizable sources of assimilable carbon for the production of the antibiotic are very diverse, there being included sugars (for example, glucose, D-fructose, D-mannitol, maltose, arabinose, rhamnose, raffinose, xylose, and the like), dextrin, starches of different types of origin, glycerol (and other polyalcohols), inositol and animal and vegetable fats, as well as esters thereof. The sources of organic assimilable nitrogen which actively stimulate growth and favor production of AY24,668 are substances such as soybean meal, cotton meal and other vegetable meals (whole or partially or totally defatted), meat flours or animal viscera, various peptones, casein hydrolysates, soybean hydrolysates, yeast hydrolysates, lactalbumin, wheat glutins, distillers solubles, corn steeps, molasses, urea and amino acids.

Mineral salts, such as the chlorides, nitrates, sulfates, carbonates and phosphates of sodium, potassium, ammonium and calcium, should be included in appropriate concentrations. The nutritive medium should contain a number of trace elements such as magnesium, iron, manganese, and zinc.

The inoculum of the above medium for the fermentation is provided with a fresh slant of *Streptomyces hygroscopicus* NRRL 5491.

Under the described conditions and with the temperature of cultivation at about 20° to 35° C., preferably at about 25° C., maximum production of AY24,668 in tanks is obtained in from about 2 to about 8 days. Alternatively, the pH may be controlled during fermentation in tanks and maintained at about pH 6.0, and glucose may be added continuously from about 2 days after beginning to the end of fermentation, thus obtaining maximum yields in about 4 to 5 days.

Thereafter, a variety of procedures may be employed in the isolation and purification of AY24,668, for example, solvent extraction, partition chromatography, silica gel chromatography, liquid-liquid distribution in a Craig apparatus, and crystallization from solvents. Solvent extraction procedures are preferred for commercial recovery inasmuch as they are less time consuming and less expensive.

Generally speaking, AY24,668 may be harvested by one of the following methods.

a. The fermentation mixture is extracted with a substantially water-immiscible solvent, preferably a lower alkanol, for example, n-butanol, n-pentanol, a commercial mixture of pentanols, or n-hexanol, or a substantially water-immiscible lower alkyl lower alkanoate, for example, ethyl acetate, butyl acetate, amyl acetate or the commercially available mixture of amyl acetates, or a substantially water-immiscible halogenated aliphatic hydrocarbon, for example, chloroform, methylene dichloride or dichloroethane. The extracts are dried and concentrated under reduced pressure to yield an oily residue which is in turn extracted with a water-miscible solvent, preferably a lower alkanol, for example methanol or ethanol. Said last-named extracts are filtered through diatomaceous earth and the filtrate concentrated under reduced pressure to yield an oily residue containing crude AY24,668.

b. The fermentation mixture is filtered through a pad of diatomaceous earth and the filter cake containing the mycelium is extracted as described below under (c). The filtrate, ie. the mycelium-free fermentation mixture, is extracted several times with a substantially water-immiscible solvent, for example, a lower alkanol, lower alkyl lower alkanoate or halogenated aliphatic hydrocarbon as exemplified above in section (a). The extracts are dried and concentrated under reduced pressure to yield an oily residue which is extracted with a water-miscible solvent, preferably a lower alkanol, for example methanol or ethanol. Said last-named extracts are treated in the same manner as described above under (a) to yield an oily residue containing crude AY24,668.

c. The mycelium is separated from the fermentation mixture and extracted with a suitable water-miscible solvent, preferably a lower alkanol, for example methanol or ethanol. The extract is concentrated by evaporation to the aqueous phase, which in turn is extracted with a substantially water-immiscible solvent, such as a lower alkyl lower alkanoate, halogenated aliphatic hydrocarbon or a substantially water-immiscible lower alkanol as described above or an aromatic hydrocarbon, for example benzene or toluene. The latter extract is evaporated under reduced pressure to yield an oily residue containing crude AY24,668.

The crude AY24,668 obtained by any of the processes described in sections (a), (b) or (c) is then purified by a variety of methods, for example, see above. Preferred methods include absorption of the crude AY24,668 on an absorbent, for instance charcoal or silica gel from a solution in a substantially non-polar, first solvent, followed by elution therefrom with a second solvent, more polar than said first solvent.

AY24,668 is used as an antifungal agent against pathogenic fungi, for example *Candida albicans*.

The inhibitory activity of AY24,668 is especially pronounced against *Candida albicans* and said last organism may be used advantageously for assay purposes.

The antifungal activity of this compound is demonstrable in standard tests used for this purpose, for example, in the tests described in "Antiseptics, Disinfectants, Fungicides and Sterilization," G. F. Reddish, Ed., 2nd ed., Lea and Febiger, Philadelphia, 1957 or by D. C. Grove and W. A. Randall in "Assay Methods of Antibiotics," Med. Encycl. Inc., New York 1955.

When AY24,668 is employed as an antifungal agent in warm blooded animals, e.g. rats, it may be used alone or in combination with pharmaceutically acceptable carriers, the proportion of which is determined by the solubility and chemical nature of the compound, chosen route of administration and standard biological practice. For example, an antifungal effective amount of AY24,668 may be administered orally in solid form containing such excipients as starch, sugar, certain types of clay and so forth. Similarly, such an amount may also be administered orally in the form of solutions or suspensions, or AY24,668 may be injected parenterally. For parenteral administration AY24,668 may be used in the form a sterile solution or suspension containing other solutes or suspending agents, for example, enough saline or glucose to make the solution isotonic, bile salts, acacia, gelatin, sorbitan monooleate, polysorbate 80 (oleate esters of sorbitol and its anhydrides copolymerized with ethylene oxide), polyoxyethylated fatty acids, polyoxyethylated alcohols, polyoxyethylated glycerin hydroxy fatty acids and the like.

The dosage of AY24,668 as an antibiotic will vary with the form of administration. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compound of this invention is most desirably administered at a concentration level that will generally afford antifungally effective results without causing any harmful or deleterious side effects and preferably at a level that is in a range of from about 2.0 mg to about 250 mg per kilo per day, although as aforementioned variations will occur. However, a dosage level that is in the range of from about 20 mg to about 100 mg per kilo per day is most desirably employed in order to achieve effective results.

In addition, AY24,668 may be employed topically as an antifungal agent. For topical application it may be formulated in the form of solutions, creams, or lotions in pharmaceutically acceptable vehicles containing 0.1-5 percent, preferably 2 percent of the agent, and may be administered topically to the infected area of the skin.

AY24,668 may also be used for cleaning and disinfecting laboratory equipment, surgical instruments, locker rooms, or shower rooms of sensitive fungus organisms. For such purposes it is preferred to use 0.1-10% solutions of AY24,668 in a lower alkanol, preferably methanol, diluted with 10-100 volumes of water containing 0.001-0.1% of a non-ionic surface-active agent, for example, polysorbate 80 U.S.P., immediately before applying it to the objects to be cleaned and disinfected.

PREPARATION

In one embodiment of this invention AY24,668 is prepared in the following manner:

A suitable fermenter is charged with production medium 8 KM (see Example 1). After sterilization and cooling, the medium is inoculated with a first stage inoculum preparation of *Streptomyces hygroscopicus* NRRL 5491.

A maximum titre of 5 to 20 μg/ml of the antibiotic is reached in the fermentation mixture after 2-8 days, usually after about 5 days, as determined by the cup plate method and *Candida albicans* as the test organism. The mycelium is harvested by filtration with diatomaceous earth. AY24,668, is then extracted from the mycelium with a water-miscible solvent, for example a lower alkanol, preferably methanol or ethanol. The latter extract is then concentrated, preferably under reduced pressure, and the resulting aqueous phase is extracted with a water-immiscible solvent. A preferred water-immiscible solvent for this purpose is methylene dichloride although chloroform, carbon tetrachloride, benzene, n-butanol and the like may also be used. The latter extract is concentrated, preferably under reduced pressure, to afford the crude product as an oil.

The product may be purified further by a variety of methods. Among the preferred methods of purification is to dissolve the crude product in a substantially nonpolar, first solvent, for example petroleum ether or or hexane, and to treat the resulting solution with a suitable absorbent, for example charcoal or silica gel, so that the antibiotic becomes absorbed on the absorbant. The absorbant is then separated and washed or preferably eluted with a second solvent more polar than the first solvent, for example ethyl acetate, methylene dichloride, or preferably a mixture of methylene dichloride and diethyl ether. Thereafter, concentration of the wash solution or eluate affords substantially pure AY24,668. Further purification is obtained by partial precipitation with a nonpolar solvent, for example, petroleum ether, hexane, pentane and the like, from a solution of the AY24,668 in a more polar solvent, for example, diethyl ether, ethyl acetate, benzene and the like. Still further purification is obtained by column chromatography, preferably employing silica gel, and by crystallization of the AY24,668 from diethyl ether.

In another preferred embodiment of this invention a first stage inoculum of *Streptomyces hygroscopicus* NRRL 5491 is prepared in small batches in a medium containing soybean flour, glucose, ammonium sulfate, and calcium carbonate incubated at about 25° C. at pH 7.1-7.3 for 24 hrs with agitation, preferably on a gyrotary shaker. The growth thus obtained is used to inoculate a number of somewhat larger batches of the same medium as described above which are incubated at about 25° C. and pH 7.1-7.3 for 18 hrs with agitation, preferably on a reciprocating shaker, to obtain a second stage inoculum which is used to inoculate the production stage fermenters.

The production stage fermenters are equipped with devices for controlling and maintaining pH at a predetermined level and for continuous metered addition of nutrient. They are charged with a medium containing soybean flour, glucose, ammonium sulfate, and potassium phosphate, sterilized, and the pH is adjusted to pH 5.8-6.2. The fermenters are inoculated with the second stage inoculum described above and incubated at about 20° to 35° C., preferably 30° to 35° C., with agitation and aeration while controlling and maintaining the mixture at approximately pH 6.0 by addition of a base, for example, sodium hydroxide, potassium hydroxide or preferably ammonium hydroxide, as required from time to time. Addition of a source of assimilable carbon, preferably glucose, is started when the concentration of the latter in the broth has dropped to about 0.5% wt/vol, normally about 48 hrs after the start of fermentation, and is maintained until the end of the particular run. In this manner a fermentation broth containing about 10 μg/ml of AY24,668, as determined by the assay method described above, is obtained in 4-5 days, when fermentation is stopped.

Rapamycin is also coproduced and present in the fermentation broth, see U.S. Pat. No. 3,929,992, cited above. The amount of coproduced rapamycin can be reduced by conducting the incubation at 30° to 35° C.

Filtration of the mycelium, mixing the latter with a water-miscible lower alkanol, preferably methanol, followed by extraction with a halogenated aliphatic hydrocarbon, preferably trichloroethane, and evaporation of the solvents yields a first oily residue. This first oily residue is dissolved in a lower aliphatic ketone, preferably acetone, filtered from insoluble impurities, the filtrate evaporated to yield a second oily residue which is extracted with a water-miscible lower alkanol, preferably methanol, and the latter extracts evaporated to yield crude AY24,668 as a third oily residue. This third oily residue is dissolved in a mixture of a lower aliphatic ketone and a lower aliphatic hydrocarbon, preferably acetone-hexane, an absorbent such as charcoal or preferably silica gel is added to adsorb the AY24,668, the latter is eluted from the adsorbate with a similar but more polar solvent mixture, for example a mixture as above but containing a higher proportion of the aliphatic ketone, the eluates are evaporated and the residue is crystallized from diethyl ether, to yield pure crystalline AY24,668. In this manner a total of 45-58% of the AY24,668 initially present in the fermentation mixture is recovered as pure crystalline AY24,668.

Figure 2:
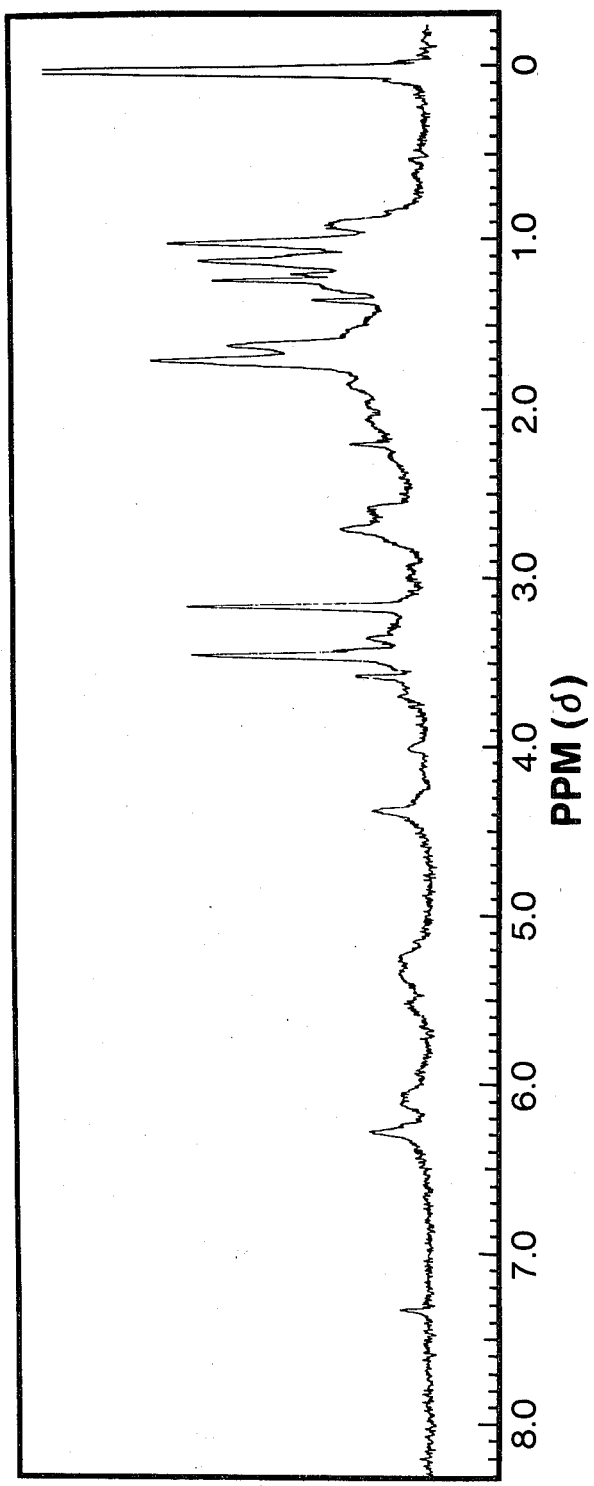

CHARACTERIZATION a. Purified AY24,668 is a solid which gives a colorless crystalline compound, mp 122°-124° C. after recrystallization from diethyl ether;

b. AY24,668 is soluble in diethyl ether, chloroform, acetone, methanol and dimethylformamide; very sparingly soluble in hexane and petroleum ether and substantially insoluble in water;

c. AY24,668 shows a uniform spot on thin layer plates of silica gel G (E. Merck. A.G., Darmstadt) developed with a variety of thin layer chromatography solvent systems; for example, diethyl ether-hexane 40:60 (Rf=0.48), isopropyl alcohol-benzene 15:85 (Rf=0.6) and ethanol-benzene 20:80 (Rf=0.5); the ratios for the solvent systems being expressed as v/v;

d. AY24,668 obtained from two successive fermentation batches gave the following values on repeated elemental analyses:

|     |       |       | AVERAGE |
| --- | ----- | ----- | ------- |
| C % | 67.86 | 67.64 | 67.75   |
| H % | 8.94  | 8.92  | 8.93    |
| N % | 1.68  | 1.75  | 1.72    | e. AY24,668 exhibits the following characteristic absorption maxima in its ultraviolet absorption spectrum (95% v/v ethanol):

267 nm($E_{1cm}^{1\%}$ 421), 277 nm ($E_{1cm}^{1\%}$ 549) and 288 nm ($E_{1cm}^{1\%}$ 423);

f. the infrared absorption spectrum of AY24,668 in chloroform is reproduced in FIG. 1 and shows characteristic absorption bands at 3500, 3010, 3000, 2935, 2870, 1735, 1712, and 1640 cm$^{-1}$.

g. the nuclear magnetic resonance spectrum of AY24,668 in deuterochloroform is reproduced in FIG. 2, and shows 0.9, 1.0, 1.1, 1.2, 1.25, 1.35, 1.6, 1.7, 2.2, 2.5, 2.7, 3.175, 3.35, 3.45, 3.6, 4.0, 4.4, 6.32 and 7.32 $\delta$;

h. The minimum inhibitory concentration of AY24,668 against various microorganism is 0.36 to 10 μg/ml for *Candida albicans* (5 strains) and 2.5 μg/ml for *C. pseudotropicalis*;

i. AY24,668 exhibits a $LD_{50}$(i.p., mice) of >900 mg/kg and a $LD_{50}$(i.p., guinea pig) of >100 mg/kg.

In protection studies, mice were infected by intravenous injection of *C. albicans* ATCC 11651. At 1, 4 and 24 hours after injection, mice were administered 20 mg/kg (s.c.) of AY24,668. At this dose 50% of the mice were protected. Treatment with 25 mg/kg (s.c.) offered complete protection.

A 1% suspension (0.2 ml) of AY24,668 in water containing 1.5% polysorbate 80 (Tween 80), when injected intradermally into a rabbit's ear caused no irritation. Similarly, two drops of a 0.5% suspension applied to a rabbit's eye caused no irritation.

The following Examples illustrate further this invention.

EXAMPLE 1

Microorganism

*Streptomyces hygroscopicus* NRRL 5491 was grown and maintained on oatmeal-tomato paste of agar slants (T. G. Pridham, et al., Antibiotic Annual 1956–1957, Medical Encyclopedia Inc., New York. p. 947) and in Roux bottles containing the same medium. Good growth was obtained after 7 days of incubation at 28° C. Spores from one Roux bottle were washed off and suspended into 50 ml of sterile distilled water. This suspension was used to inoculate the first stage inoculum.

The first stage inoculum medium consisted of Emerson broth [R. L. Emerson et al., J. Bacteriol, 52, 357 (1946)] beef extract, 0.4%; peptone, 0.4%; sodium chloride, 0.25%; yeast extract, 0.1%; and glucose, 1%; pH 7.0; flasks containing the above medium were inoculated with 1% of the spore suspension described above. The inoculated flasks were incubated for 30 hrs. at 28° C. on a reciprocating shaker set at 65 r.p.m. (4 inch stroke).

Production Stage

The production stage was run in 250-liter New Brunswick fermenters Model F-250, equipped with automatic antifoam addition system and pH recorder-controller. The fermenters were charged with 160 liters of an aqueous production medium (8 KM) consisting of the following constituents:

| soluble starch | 1.0% |
| --- | --- |
| (NH$_4$)$_2$SO$_4$ | 0.5% |
| K$_2$HOP$_4$ | 0.5% |
| glucose (Cerelose TM) | 1.5% |
| MgSO$_4$ | 0.025% |
| ZnSO$_4$ | 0.005% |
| MnSO$_4$ | 0.001% |
| FeSO$_4$7H$_2$O | 0.002% |
| CaCO$_3$ | 0.2% |
| "Blackstrap" molasses | 0.5% |
| hydrolyzed casein (NZ-Case, Sheffield Chemical, Norwich, New York) | 0.5% |
| lard oil (Larex No. 1, Swift Canadian Co., Toronto) pH 7.1 to 7.3 | 0.2% |

The fermenters were sterilized at 121° C. for 45 minutes, cooled and inoculated with one flask (2% inoculum) of first stage inoculum. Incubation temperature: 28° C.; aeration: 0.5 vol/vol/min.; agitation; 250 r.p.m.

A titre of ca. 20 μg/ml, determined by microbiological assay on agar plates seeded with *Candida albicans* was reached in 5 days. The fermentation was stopped.

Extraction and isolation of the antibiotic was performed by one of the following methods:

Extraction a. The fermentation mixture was extracted twice with 1 v/v of n-butanol. The combined butanol extracts were washed with 1 v/v of water, dried with anhydrous sodium sulfate and evaporated to dryness under reduced pressure to yield a residue. The oily residue was extracted 3 times with 2 liters of methanol. The combined methanol extracts were passed through diatomaceous earth (Celite TM) and evaporated to dryness to yield an oily residue containing crude AY24,668 and rapamycin.

b. The fermentation mixture was filtered over diatomaceous earth (Celite TM). The filtrate was extracted twice with 1 v/v of ethyl acetate. The ethyl acetate extracts were washed with 1 volume of water, dried with anhydrous sodium sulfate and evaporated under reduced pressure to dryness. The residue was extracted twice with 1 liter of methanol. The methanol extracts were evaporated under reduced pressure to yield an oily residue containing crude AY24,668 and rapamycin.

c. The mycelium obtained as described under section (b) was washed with 1 to 2 volumes of water. The washed mycelium was extracted 3 times with 5 volumes of methanol per weight of wet mycelium each time. The methanolic extracts were pooled and concentrated under reduced pressure to a small volume of an aqueous phase containing approximately 10% v/v of methanol. This aqueous phase was extracted 3 times with 1 vol. of methylene chloride; the methylene chloride extracts were combined, dried with anhydrous sodium sulfate and evaporated to yield an oily residue.

The oily residue, obtained by any of the extraction procedures described above, was diluted with 1 volume of petroleum ether, and 30% w/v of charcoal (Darco G60 TM ) was added. The mixture was stirred for half an hour and filtered. The charcoal, which retained substantially all of the product, was washed twice with one volume of petroleum ether. The charcoal was eluted three times with 5 vol. (based on the weight of the charcoal) of a mixture of methylene chloride and diethyl ether (50:50). The methylene chloride-diethyl ether extracts were evaporated to dryness and the residue was dissolved in a small amount of diethyl ether. The crude rapamycin was obtained by precipitation from the diethyl ether solution with cold petroleum ether whereas AY24,668 remained with the mother liquors.

Alternatively, the oily residue, obtained by any of the extraction procedures described above, was diluted with 1 vol. of hexane and passed through a preparative column of silica gel G. The product was adsorbed on the column. The silica gel G containing adsorbed product was washed with several volumes of hexane and 50:50 hexane-diethyl ether mixtures. The product was eluted from the column with diethyl ether. The ether eluant was evaporated to a small volume and crude rapamycin obtained by precipitation from a diethyl ether solution with cold petroleum ether. The product AY24,668 remained with the mother liquor.

Purification

The forementioned mother liquors obtained from many fermentation runs were combined and subjected to column chromatography on silica gel G Merck (50:1 w/v) in hexane-diethyl ether (50:50). The product, identified by its Rf value—see hereinbefore, was eluted from the column with diethyl ether. The ether eluate was evaporated to a small volume. Purified AY24,668 was precipitated with petroleum ether. The analytical samples were prepared by crystallization from diethyl ether m.p. 122°–124° C.

EXAMPLE 2

Streptomyces hygroscopicus NRRL 5491 is grown and spores are obtained in the same manner as described in Example 1.

First Stage Inoculum. Erlenmeyer flasks (500 ml) are filled with 100 ml of the following medium:

| Soybean flour (Archer-Daniels Co. Midland, Mich. "Special X") | = | 4% wt/vol |
|---|---|---|
| Glucose (Cerelose TM ) | = | 2% wt/vol |
| Ammonium sulfate | = | 0.3% wt/vol |
| Calcium carbonate | = | 0.15% wt/vol |
| Water to volume, pH 7.1 to 7.3 | | |

The flasks are sterilized at 121° for 35 minutes and cooled to 25°. The flasks are inoculated with 4% (4 ml) of spore suspension described above and incubated on a gyrotary shaker (2 inch stroke) at 240 rpm for 24 hrs at 25° C.

Second Stage Inoculum: Twenty-four liter flat bottom flasks containing 3.2 l of the inoculum medium described above at pH 7.1–7.3 are sterilized by autoclaving at 121° for 35 minutes, shaken to resuspend the insoluble material and resterilized for another 45 minutes. The flasks are cooled to 25° and inoculated with 64 ml of first stage inoculum, placed on a reciprocating shaker (4 inch stroke) set at 65 rpm and incubated for 18 hrs at 25° C.

Production Stage: The production stage is run in 250 liter New Brunswick fermenters Model F-250 equipped with automatic antifoam addition system and pH recorder-controller. The fermenters are charged with 160 liters of an aqueous production medium consisting of the following constituents:

| Soybean flour (Archer-Daniels Co., Midland, Mich., "Special X") | = | 3% wt/vol |
|---|---|---|
| Glucose (Cerelose TM ) | = | 2% wt/vol |
| Ammonium sulfate | = | 0.1% wt/vol |
| Potassium phosphate (monobasic) | = | 0.5% wt/vol |
| Antifoaming Agent ("DF-143-PX" Mazer Chemicals, Inc., Gurnee, Ill.) | = | 0.05% wt/vol |

The fermenters are sterilized at 121° C. for 30 minutes, cooled, and the pH is adjusted to 5.8 to 6.2 with ammonium hydroxide. They are then inoculated with one flask (2%) of second stage inoculum and fermentation is allowed to proceed at 25° C., with aeration at 0.25 v/v/min and agitation at 200 rpm.

The pH of the fermentation broth starts to drop at 30–35 hours and is controlled at 6.0 until the end of fermentation by the automatic, on demand, addition of ammonium hydroxide. At about 48 hrs of propagation the glucose concentration in the broth drops to about 0.5% and continuous addition of 40% glucose solution is started at a rate of 3.75% of fermentation mixture volume per day and continued until the end of fermentation. A titer of about 60 μg/ml (combined activity of rapamycin and AY24,668), determined by microbiological assay on agar plates seeded with Candida albicans is reached in 4 to 5 days. The fermentation is stopped at this point.

Extraction and isolation of AY24,668 is performed by the following procedure:

The fermentation mixture is filtered over diatomaceous earth to recover the mycelium. A typical 400 liter batch obtained from three fermenters yields about 60 kg of wet mycelium. The wet mycelium is mixed with 1 vol/wt of methanol by agitation and the mixture is extracted twice with 2 vol of trichloroethane (methyl chloroform), yielding about 250 liters of trichloroethane extract containing about 4 to 5 g of a mixture of AY24,668 and rapamycin. The trichloroethane extract is evaporated to dryness under reduced pressure to yield 1 to 1.4 kg of oily residue. This residue is added slowly with agitation to 5 vols of acetone and the resulting precipitate is separated by filtration. The acetone solution is evaporated to dryness under reduced pressure to yield an oily residue. This oily residue is extracted twice with 2 and 1 vols of methanol respectively. The combined methanol extracts are filtered and the remaining oil is discarded. The methanol extract containing AY24,668 and rapamycin is evaporated to dryness under reduced pressure to yield 200 to 300 g of oily residue. This residue is dissolved in 5 v/wt of 15% acetone in hexane. To this solution of the oily residue, silica gel (Merck) is added in an amount equal to twice the weight of the oily residue and the mixture is stirred for about 1 hr. The mixture is filtered on a sintered glass funnel and the filtrate is rejected. The silica gel containing AY24,668 and rapamycin is washed with several volumes of 15% acetone in hexane. The washed silica gel is eluted with 30% acetone in hexane. The appropriate fraction of eluant, as indicated by Rf values, are evaporated to dryness to yield about 8 to 12 g of dry residue. The dry residue is dissolved in diethyl ether and rapamycin is separated by crystallization. The crystallization mother liquors, which are now rich in AY24,668, are combined from several runs and subjected to silica gel G column chromatography in 20% (v/v) acetone in hexane. The fractions containing AY24,668 (as determined by TLC) are combined and evaporated to dryness. The residue is dissolved in diethyl ether and AY24,668 is separated by crystallization. Typically, mother liquors from 4 or 5 fermentation runs (1,600–2,000 liters of fermentation broth) yields about one gram of pure AY24,668.

EXAMPLE 3

The procedure of Example 2 is repeated with the fermentation (production stage) being run at 33° to 34° C. At this temperature, the production of rapamycin is greatly suppressed and the major antifungal agent produced by the microoganism is AY24,668. A titre of 7 μg/ml of AY24,668 is obtained in 6 days. The extraction and recovery procedures are the same as described in Example 2. A typical 400 liter fermentation run yields about 1.2 g of AY24,668. By this modification in fermentation temperature, AY24,668 is recovered without interference from rapamycin.

We claim:

1. Solid AY24,668, an antibiotic which
  a. gives a colorless, crystalline compound with a melting point of 122° to 124° C., after recrystallization from diethyl ether;
  b. is soluble in diethyl ether, chloroform, acetone, methanol and dimethylformamide, very sparingly soluble in hexane and petroleum ether and substantially insoluble in water;
  c. shows a uniform spot on thin layer plates of silica gel;
  d. has a characteristic elemental analysis of about C, 67.75%, H, 8.93% N, 1.72%;
  e. exhibits the following characteristic absorption maxima in its ultraviolet absorption spectrum (95% ethanol): 267 nm ($E_{1cm}^{1\%}$ 421), 277 nm ($E_{1cm}^{1\%}$ 549) and 288 nm ($E_{1cm}^{1\%}$ 423);
  f. has a characteristic infrared absorption spectrum shown in accompanying FIG. 1;
  g. has a characteristic nuclear magnetic resonance spectrum as shown in accompanying FIG. 2;
  h. has a minimum inhibitory concentration of 0.36 to 10.0 μg/ml against *Candida albicans;* and
  i. exhibits a $LD_{50}$(i.p., mice) of >900 mg/kg.

2. A pharmaceutical composition which comprises a pharmaceutically acceptable carrier and an antifungal effective amount of the antibiotic AY24,668 which
  a. is a solid giving a colorless, crystalline compound with a melting point of 122° to 124° C., after recrystallization from diethyl ether;
  b. is soluble in diethyl ether, chloroform, acetone, methanol and dimethylformamide, very sparingly soluble in hexane and petroleum ether and substantially insoluble in water;
  c. shows a uniform spot on thin layer plates of silica gel;
  d. has a characteristic elemental analysis of about C, 67.75%, H, 8.93% N, 1.72%;
  e. exhibits the following characteristic absorption maxima in its ultraviolet absorption spectrum (95% ethanol): 267 nm ($E_{1cm}^{1\%}$ 421), 277 nm ($E_{1cm}^{1\%}$ 549) and 288 nm ($E_{1cm}^{1\%}$ 423);
  f. has a characteristic infrared absorption spectrum shown in accompanying FIG. 1;
  g. has a characteristic nuclear magnetic resonance spectrum as shown in accompanying FIG. 2;
  h. has a minimum inhibitory concentration of 0.36 to 10.0 μg/ml against *Candida albicans;* and
  i. exhibits a $LD_{50}$ (i.p., mice) of >900 mg/kg.

3. A method of inhibiting the growth of pathogenic fungi in a mammal which comprises administering to the mammal an antifungally effective amount of the antibiotic AY24,668 which
  a. is a solid giving a colorless, crystalline compound with a melting point of 122° to 124° C., after recrystallization from diethyl ether;
  b. is soluble in diethyl ether, chloroform, acetone, methanol and dimethylformamide, very sparingly soluble in hexane and petroleum ether and substantially insoluble in water;
  c. shows a uniform spot on thin layer plates of silica gel;
  d. has a characteristic elemental analysis of about C, 67.75%, H, 8.93% N, 1.72%;
  e. exhibits the following characteristic absorption maxima in its ultraviolet absorption spectrum (95% ethanol): 267 nm ($E_{1cm}^{1\%}$ 421), 277 nm ($E_{1cm}^{1\%}$ 549) and 288 nm ($E_{1cm}^{1\%}$ 423);
  f. has a characteristic infrared absorption spectrum shown in accompanying FIG. 1;
  g. has a characteristic nuclear magnetic resonance spectrum as shown in accompanying FIG. 2;
  h. has a minimum inhibitory concentration of 0.36 to 10.0 μg/ml against *Candida albicans;* and
  i. exhibits a $LD_{50}$ (i.p., mice) of >900 mg/kg.

* * * * *